United States Patent [19]
Markwell

[11] 4,428,940
[45] Jan. 31, 1984

[54] ANTI-HYPERTENSIVE COMPOUNDS AND COMPOSITIONS
[75] Inventor: Roger E. Markwell, Great Dunmow, England
[73] Assignee: Beecham Group p.l.c., England
[21] Appl. No.: 356,445
[22] Filed: Mar. 9, 1982
[30] Foreign Application Priority Data
Mar. 12, 1981 [GB] United Kingdom ................ 8107837
[51] Int. Cl.$^3$ ..................... A61K 37/00; A01N 43/78
[52] U.S. Cl. .................................. 424/177; 424/270; 548/201; 548/525
[58] Field of Search ............... 548/201, 525; 424/177, 424/270
[56] References Cited
U.S. PATENT DOCUMENTS 4,192,878  3/1980  Ondetti ................ 548/201
4,282,235  8/1981  Ondetti ................ 548/201
4,308,392 12/1981  Petrillo, Jr. et al. ...... 548/201
4,371,699  2/1983  Ohashi et al. ........... 548/201

FOREIGN PATENT DOCUMENTS 12401  6/1980  European Pat. Off. ..... 260/112.5 R

Primary Examiner—Delbert R. Phillips
Attorney, Agent, or Firm—Jacobs & Jacobs

[57] ABSTRACT

Compounds of formula (I):

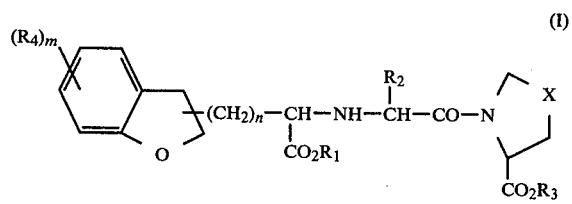

or a pharmaceutically acceptable salt thereof, wherein
m is 0 to 3;
n is 1 to 5;
$R_1$ is hydrogen, or $C_{1-6}$ alkyl;
$R_2$ is hydrogen, $C_{1-4}$ alkyl, $-(CH_2)_p-NH_2$ wherein p is 1 to 4, or $-NHCOR$, wherein $R_5$ is $C_{1-4}$ alkyl;
$R_3$ is hydrogen or $C_{1-6}$ alkyl;
$R_4$ is $C_{1-4}$ alkyl, $C_{1-4}$ alkoxy, halogen or $CF_3$; and X is $CH_2$ or S.

having useful pharmacological activity, compositions containing them, and a process for their preparation.

13 Claims, No Drawings

ANTI-HYPERTENSIVE COMPOUNDS AND COMPOSITIONS

This invention relates to novel compounds having pharmacological activity, to pharmaceutical compositions containing them, and to a process for their preparation.

Captopril is a known compound having anti-hypertensive activity and the formula (A):

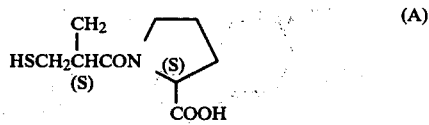

European Patent Publication No. 12401 describes a class of compounds which also have anti-hypertensive activity and which differ from captopril by the replacement of the $HSCH_2$—moiety by a group of formula (B):

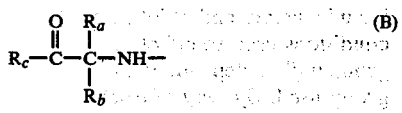

wherein $R_a$ is hydrogen, alkyl, substituted lower alkyl, substituted or unsubstituted aryl, substituted or unsubstituted arylloweralkyl arylloweralkyl, heteroarylloweralkyl or heteroarloweralkenyl, or aryllloweralkyl or heteroarylloweralkyl substituted on the alkyl position, and $R_b$ is hydrogen or lower alkyl, and $R_c$ is hydroxy or alkenoxy or alkoxy, aryloxy, or amino, each of which may be optionally substituted. A representative compound disclosed in the European Patent Publication has formula (C):

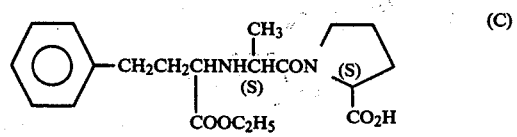

and is referred to as N-(1(s)-ethoxycarbonyl-3-phenylpropyl)-L-alanyl-L-proline.

A novel class of compounds has now been discovered which also has antihypertensive activity.

Accordingly the present invention provides a compound of formula (I):

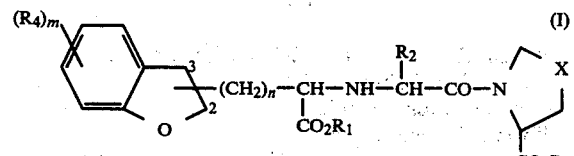

or a pharmaceutically acceptable salt thereof, wherein
m is 0 to 3;
n is 1 to 5;
$R_1$ is hydrogen, or $C_{1-6}$alkyl;
$R_2$ is hydrogen, $C_{1-4}$alkyl, —$(CH_2)_p$—$NH_2$ wherein p is 1 to 4, or —$NHCOR_5$ wherein $R_5$ is $C_{1-4}$ alkyl;
$R_3$ is hydrogen or $C_{1-6}$alkyl;
$R_4$ is $C_{1-4}$alkyl, $C_{1-4}$alkoxy, halogen or $CF_3$; and
X is $CH_2$ or S.

The dihydrobenzofuranyl moiety may be bonded to the rest of the structure at the 2- or 3-position, preferably, the 2-position.

Suitable examples of m are 0, 1 and 2, preferably 0.

Suitable examples of n are 1 and 2. Preferred ranges of n within the generality of the invention are 2 to 5 and 2 to 4. Specific examples are 2 and 3.

Suitable examples of $R_1$ and $R_3$ are hydrogen, methyl, ethyl and n- and iso-propyl. Often $R_3$ will be hydrogen and $R_1$ will be hydrogen or alkyl, such as ethyl.

Suitable examples of $R_2$ include hydrogen, methyl, ethyl, n- and iso-propyl, more suitably hydrogen or methyl. $R_2$ may also suitably be —$(CH_2)_p$—$NH_2$ with p suitably being 1 or 2; p is 4 is also a suitable value.

Suitable examples of $R_4$ include methyl, ethyl; methoxy, ethoxy; chloro, bromo and iodo; and $CF_3$.

Preferably X is $CH_2$.

The pharmaceutically acceptable salts of the compounds of formula (I) include those with bases, such as alkali metal and alkaline earth metal salts, for example sodium and potassium salts, and ammonium salts, and those with acids such as hydrochloride, hydrobromide, sulphate, phosphate, maleate and like salts.

From the aforesaid it will be appreciated that a preferred class of compounds of formula (I) is of formula (I)':

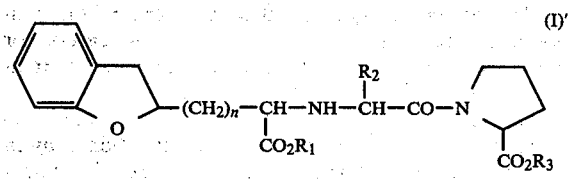

or a pharmaceutically acceptable salt thereof, wherein:
n is 1 or 2 to 5, especially 2 or 3;
$R_1$ and $R_3$ are the same or different and each is hydrogen or $C_{1-4}$alkyl, such as ethyl; and
$R_2$ is hydrogen or $C_{1-4}$alkyl, such as methyl.

The most preferred class of compounds of formula (I) are those of formula (I)', or a pharmaceutically acceptable salt thereof, wherein:
n is 2 to 5, especially 2 or 3;
$R_1$ is $C_{1-4}$alkyl, such as ethyl;
$R_2$ is $C_{1-4}$alkyl, such as methyl; and
$R_3$ is hydrogen.

The compounds of the formula (I) are inhibitors of angiotensin converting enzyme, and thus have antihypertensive activity. They may accordingly be used in the therapy of hypertension in mammals including humans.

Accordingly the present invention also provides a pharmaceutical composition, which comprises a compound of the formula (I), or in particular of formula (I)'; and a pharmaceutically acceptable carrier.

The compositions of this invention are most suitably adapted for oral administration although adaption for other modes of administration, for example by injection, are also possible.

In order to obtain consistency of administration it is preferred that the compositions of this invention are in the form of a unit-dose. Suitable unit-dose forms include tablets, capsules, ampoules and powders in sachets. Such unit dose forms aptly contain from 1 to 100 mg of a compound of this invention and more usually from 2 to 75 mg, for example 5 to 50 mg.

Such compositions may be administered from 1 to 6 times a day, more usually from 2 to 4 times a day, in a regimen such that the daily dose is from 5 to 200 mg for a 70 kg human adult and preferably from 10 to 100 mg.

The compositions of this invention may be formulated in conventional manner, for example in a manner similar to that used for known antihypertensive agents such as hydrallazine.

In addition such compositions may contain further active agents such as other anti-hypertensive agents especially β-blocking agents, and diuretics.

The invention also provides a process for the preparation of a compound of formula (I) which comprises the reduction of a compound of formula (II):

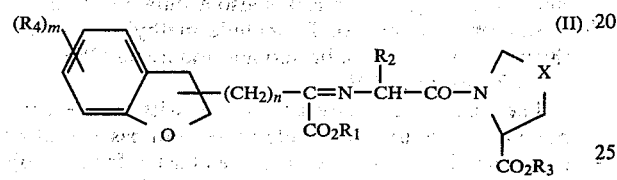

wherein $R_1$ to $R_4$ and m and n are as defined for formula (I) or (I)'.

The reduction is carried out in any suitable manner known generally for such reductions. For example, sodium cyanoborohydride may be used in a suitable dry solvent, such as ethanol. Alternatively the reaction may be carried out by hydrogenation over one of the conventional catalysts, such as palladium on carbon or platinum or rhodium in a suitable dry solvent, for example ethanol.

The compounds of formula (II) which are novel intermediates and represent part of the invention, may in turn be prepared by reacting a compound of formula (III):

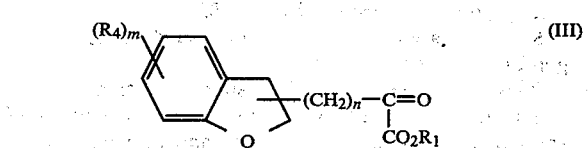

with a compound of formula (IV):

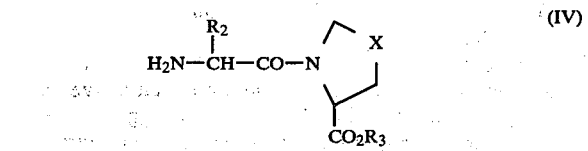

wherein $R_1$ to $R_4$ and m and n are as defined for formula (I) or (I)'.

The coupling reaction between the compounds of formulae (III) and (IV) may be carried out by mixing together the reactants in a dry solvent.

The two-step conversion of the compounds of formulae (III) and (IV) into the desired compound of formula (I) or (I)' may preferably be carried out in one operation by producing the imine of formula (III) in situ. In such cases a means for removing the water formed as a by-product of imine formation should be present, such as,
molecular sieves. The reduction of the imine and the removal of the water will drive the reaction forward to give the desired product of formula (I) or (I)', the actual amount of imine formed at any time being very small.

The compounds of formula (IV) are either known compounds or may be prepared by processes analogous to those used for structurally similar known compounds.

The compounds of the formula (III) may be prepared by the deprotection of a compound of formula (V):

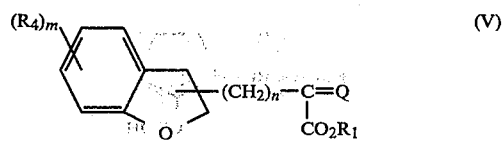

wherein Q is a carbonyl protecting group, $R_1$ is $C_{1-6}$ alkyl, and $R_4$ and m and n as defined for formula (I) or (I)', and if required, subsequently hydrolysing the compound of formula (V) to a corresponding compound of formula (V) wherein $R_1$ is hydrogen.

Suitable examples of carbonyl protecting groups Q include ketals and thioketals. Obviously the reaction conditions used to effect the removal of the protecting group will be dependent on the nature of the protecting group used. By way of example, the protecting group

is normally removed by a reaction which is carried out with either methyl iodide/acetonitrile (or acetone)/ $H_2O$, or with N-chlorosuccinimide/silver nitrate/acetonitrile/.

Compounds of formula (V) may themselves be prepared by reacting a compound of formula (VI):

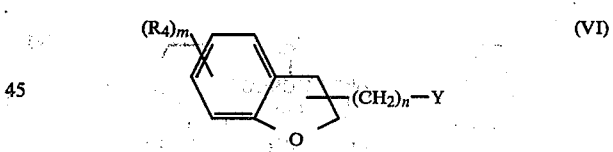

wherein Y is a leaving group, such as tosyl, mesyl and halo, for example chloro, bromo or iodo, and $R_4$, m and n are as defined for formula (I) or (I)', with a compound of formula (VII):

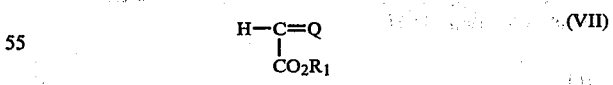

wherein $R_1$ and Q are as defined for formula (V). This reaction is suitably carried out in the presence of a strong base, for example sodium hydride in dry dimethylformamide and toluene.

Compounds of formula (VII) are either known compounds or may be prepared in an analogous manner to the preparation of structurally similar known compounds.

Compounds of formula (VI) are also known compounds or may be prepared in an analogous manner to the preparation of structurally similar, known compounds. By way of example, a modification of the literature method provided by R. Adams and R. E. Rindfusz in J. Am. Chem. Soc. 41,648 (1919) and H. Normant, Ann.Chim. 17, 335 (1942) is suitable for the preparation of those compounds of formula (VI), wherein the dihydrobenzofuranyl moiety is bonded to the rest of the structure at the 2-position, and Y is bromo and m is 0 and n is 1. This synthesis is shown below schematically:

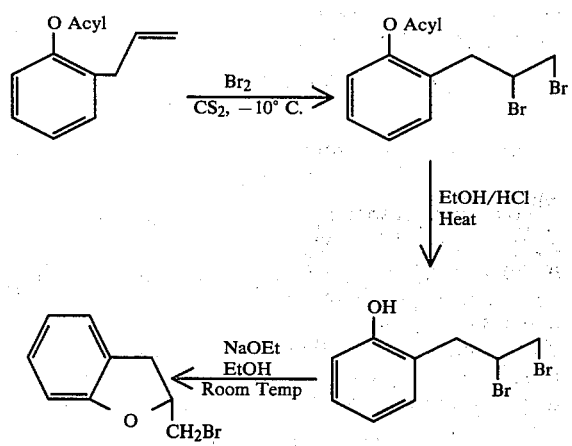

After the preparation of a compound of formula (I) or (I)' as herein described certain variable groups in the compound may then be optionally converted to other groups. By way of example, a compound of formula (I), wherein $R_1$ and $R_3$ are both hydrogen, may be esterified in conventional manner to give the corresponding compound of formula (I), wherein $R_1$ and $R_3$ are both alkyl.

The salts of the compounds of formulae (I) and (I)' may be prepared in conventional manner, for example by reacting the compound of formula (I) or (I)' with acid or base as appropriate.

The compounds of formula (I) and (I)' have asymmetric centres and thus are capable of existing in a number of stereoisomeric forms. This invention extends to each of these stereoisomeric forms and to mixtures thereof (including racemates). The different stereoisomeric forms may be separated one from the other by conventional techniques or any given isomer may be obtained by a stereospecific synthesis.

The asymmetric centres indicated by "*" in the part structures:

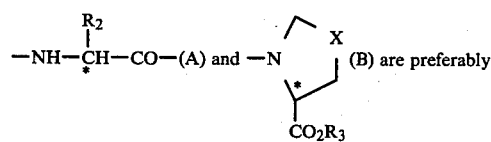

in the S configuration.

The asymmetric centres indicated by "*" in the part structures:

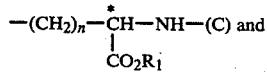

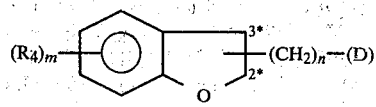

are in the R or S configuration, preferably in the S configuration in (C), or in both configurations together as in a racemic mixture.

The preferred compounds of formula (I) and (I)', are those in which the aforementioned part structures of formulae (A) to (D) are in the following configurations:

|    | (A) | (B) | (C) | (D) |
|----|-----|-----|-----|-----|
| 1. | S   | S   | R   | R   |
| 2. | S   | S   | S   | S   |
| 3. | S   | S   | R   | S   |
| 4. | S   | S   | S   | R   |
| 5. | S   | S   | RS  | RS  |

The following examples illustrate the invention.

EXAMPLE 1

(a) (2,3-Dihydro-2-benzofuranyl)-methyl bromide

A solution of bromine (90 g) in carbon disulphide (100 ml) was added dropwise to a well stirred solution of O-acetyl-2-allylphenol (100 g) in carbon disulphide (300 ml) at −10° C. over 1 hour. The solution was evaporated to dryness in vacuo, to afford O-acetyl-2-allylphenol dibromide which was immediately dissolved in dry ethanol (300 ml) containing 10 ml of a saturated ethanolic-hydrogen chloride solution. The solution was heated under gentle reflux for 2 hours, and then evaporated to dryness in vacuo. The residue was triturated with n-pentane, and the solid 2-allylphenol dibromide (135 g) was collected and washed twice with portions of n-pentane. The product is pure enough for further reaction. 2-Allylphenol dibromide (135 g) in dry ethanol (300 ml) was treated with a solution of sodium ethoxide (38 g) in ethanol (100 ml) with cooling and stirring, keeping the temperature of the reaction between 30° and 35° C. After addition, the reaction was stirred at room temperature for 1 hour, and then evaporated to dryness in vacuo. The residue was partioned between n-pentane and water. The n-pentane fraction was washed with 2% sodium hydroxide solution, water, and dried ($Na_2SO_4$). Evaporation to dryness in vacuo afforded crude (2,3-dihydro-2-benzofuranyl)-methyl bromide (90 g), which distilled at 110°–118° C./0.5 mm to afford product (78 g) of slightly higher purity.

(b) 2-[2,3-Dihydro-2-benzofuranyl) methyl]-1,3-dithane-2-carboxylic acid ethyl ester A solution of (2,3-dihydro-2-benzofuranyl) methyl bromide (22 g) and ethyl 1,3-dithiane-2-carboxylate (19.8 g) in dry DMF (50 ml) was added dropwise to a suspension of 80% sodium hydride (3.1 g) in dry toluene (50 ml) at 0° C. The mixture was stirred at room temperature for 18 hours, when water (150 ml) was added and the toluene layer separated. The aqueous fraction was further extracted with toluene; the combined toluene fractions washed with water and dried ($Na_2SO_4$). The solution was evaporated to dryness in vacuo and recrystallised from ether-pentane to afford 2-[2,3-dihydro-2- benzofuranyl) methyl]-1,3-dithiane-2-carboxylic acid ethyl ester (11.4 g), mp 71°–73° C.; M/e 324.0845 $C_{16}H_{20}O_3S_2$ requires M+ 324.0852. NMR (CDCl$_3$) δ1.25 (3H, t, J=10 Hz); 1.8–3.65 (10H, m); 4.2 (2H, q, J=10 Hz); 5.15 (1H, m); and 6.6–7.2 (4H, m).

After column chromatography on silicia gel in ethyl acetate-petroleum ether (1:9), a further batch of the compound (5.0 g) was obtained.

(c) 2,3-Dihydro-α-oxo-2-benzofuranpropanoic acid ethyl ester (i) A solution of the dithiane product of (b) (4.0 g) in acetonitrile (5 ml) was added to a solution of N-chlorosuccinimide (6.6 g) and silver nitrate (9.5 g) in 80% acetonitrile-water (50 ml) at 0° C. The temperature was allowed to rise to 15° C., and the solution was held at this temperature for 20 minutes, when a saturated aqueous solution of sodium sulphite (30 ml) was added. The aqueous solution was extracted three times with dichloromethane-hexane (1:1) (50 ml). The organic fraction was washed with sodium bicarbonate solution, then with water, and dried (Na$_2$SO$_4$). Evaporation to dryness in vacuo afforded a semi-crystalline residue which wastriturated with ether and filtered. The filtrate was evaporated to dryness in vacuo to afford 2,3-dihydro-α-oxo-2-benzofuranpropanoic acid ethyl ester (0.8 g) as a pale yellow oil; (Found m/e 234.0883, $C_{13}H_{14}O_4$ requires M+ 234.0891).

NMR (CDCl$_3$) 1.3 (3H, t, J=10 Hz); 2.5–3.5 (4H, m); 4.25 (2H, q, J=10 Hz); 5.1 (1H, m); and 6.5–7.2 (4H, m).

(ii) A solution of the dithiane product of (b) (8.5 g) in acetonitrile (40 ml) and water (10 ml) was treated with an excess of methyl iodide (26 g) under nitrogen, and the solution was well stirred at room temperature for 48 hours, and evaporated to dryness. The residue was taken in dichloromethane and washed successively with saturated sodium sulphite solution, sodium bicarbonate and water, dried over (Na$_2$SO$_4$), and evaporated to dryness. The residue was shaken with three portions of ether, which were combined and evaporated to dryness to afford a semi-crystalline solid (2.8 g) which was triturated with ether-pentane (1:1) and filtered. The filtrate was evaporated to dryness in vacuo to afford 2,3-dihydro-α-oxo-2-benzofuran propanoic acid ethyl ester (2.0 g), identical (NMR) with the previous sample.

(d) N-[N-[[2-(2,3-Dihydro-2-benzofuranyl)-1-(ethoxycarbonyl)]ethyl]-(S)-alanyl]-(S)-proline

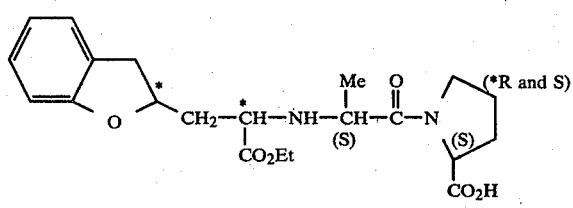

A solution of 2,3-dihydro-α-oxo-2-benzofuranpropanoic acid ethyl ester (2.0 g) in dry ethanol (15 ml) containing 4A molecular sieves (7 g) wastreated with (S)-alanyl-(S)-proline (0.7 g) and then stirred at room temperature under nitrogen for 1 hour. Sodium cyano borohydride (0.25 g) was added portionwise over 30 hours, and after 48 hours, the solution was filtered and the filtrate evaporated to dryness. The residue was partitioned between sodium bicarbonate solution and chloroform. The aqueous fraction was washed with chloroform, acidified to pH 3.5 with 10% citric acid solution, and extracted three times with chloroform. The chloroform solution was washed with water, dried (Na$_2$SO$_4$), and evaporated to dryness in vacuo to afford N-[N-[[2-(2,3-dihydro-2-benzofuranyl)-1-(ethoxycarbonyl)]ethyl]-(S)-alanyl]-(S)-proline, (0.37 g) as a pale yellow solid. Found m/e 404.1975 $C_{21}H_{28}N_2O_6$ requires M+ 404.1945.

NMR (CDCl$_3$) δ1.25 (6H,br.t); 2.1 (4H,m); 2.5–4.7 (11H,m); 4.9 (1H,m); 6.4 (2H,br.s); (exchanges with D$_2$O); and 6.6–7.2 (4H,m).

EXAMPLE 2

(a) Ethyl 2-(2,3-dihydro-2-benzofuranyl)-1-ethoxycarbonyl-propionate

To a stirred suspension of 80% sodium hydride (18.2 g-previously washed with petroleum ether) in dry dimethylformamide (500 mls) under an atmosphere of nitrogen, was added diethylmalonate (91 mls). After 30 minutes the mixture was cooled to 0° C. and (2,3-dihydro-2-benzofuranyl)methyl bromide (127 g) added maintaining the temperature below 5° C. The temperature was raised to 65° C. and the mixture heated overnight.

On cooling the solution was poured into water (3.5 l) and extracted with ether (3×500 mls). The organic phase was washed with saturated brine solution, dried over anhydrous magnesium sulphate and excess solvent removed in vacuo to yield a yellow oil (170 g). NMR (CDCl$_3$) (60 Mz) δ1.20(6H, t, J=7 Hz); 2.00–3.50 (5H, m); 4.10(4H, q, J=7 Hz); 4.65 (1H, m); 6.75 (4H, m).

(b) 2-(2,3-Dihydro-2-benzofuranyl)-1-carboxy propionic acid

A solution of ethyl 2-(2,3-dihydro-2-benzofuranyl)-1-ethoxycarbonyl-propionate (170 g), sodium hydroxide (186 g), ethanol (800 mls) and water (800 mls) was stirred at room temperature for 48 hours. The mixture was acidified with 5 N hydrochloric acid solution and extracted with ether (4×150 mls). After drying the organic phase over anhydrous magnesium sulphate, excess solvent was removed yielding a semi-solid (127 g). A sample of the product was recrystallized from ethanol, m.p. 122°–123° C. M/e 236.0691 $C_{12}H_{12}O_5$ requires M+ 236.0685, NMR (CDCl$_3$) (80 MHz) δ2.00–3.70 (5H, m); 4.75 (1H, m); 7.00 (4H, m); 9.85 (2H, s).

(c) 2-(2,3-Dihydro-2-benzofuranyl) propionic acid

A mixture of 2-(2,3-dihydro-2-benzofuranyl)-1-carboxy-propionic acid (60 g) and xylene (600 mls) was heated under reflux for 3 hours after which time most solids had dissolved. The liquid was decanted and solvent removed in vacuo yielding an oil which crystallized on standing. This product was purified by dissolving the acid in ether (200 mls) and extracting the solution with saturated sodium bicarbonate solution (3×100 mls). The bicarbonate layer was acidified with 5 N hydrochloric acid solution and the mixture extracted with ether (4×80 mls). The organic phase was dried over anhydrous magnesium sulphate and the solvent evaporated affording a white solid (35 g). M/e M+ 192. NMR (CDCl$_3$) (80 MHz) δ1.80–3.50 (6H, m); 4.75 (1H, m); 6.60–7.30 (4H, m).

(d) 3-(2,3-Dihydro-2-benzofuranyl) propanol 2-(2,3-Dihydrobenzofuranyl)-propanoic acid (10 g) was dissolved in ether (60 mls) added dropwise to a stirred suspension of lithium aluminum hydride (2.0 g) in ether (90 mls). The reaction temperature was maintained below 30° C. whilst under an atmosphere of nitrogen. After 3 hours water was added to destroy excess hydride. The mixture was filtered and the ether layer separated and dried over anhydrous magnesium sulphate. Removal of solvent gave an oil (8.0 g). M/e 178.0984 NMR (CDCl$_3$) (60 MHz) δ1.65 (4H, m); 2.30–3.30 (2H, m); 3.50 (2H, t, J=6 Hz); 3.90 (1H, s), 4.65 (1H, m); 6.40–7.20 (4H, m).

(e) 3-(2,3-Dihydro-2-benzofuranyl) propyl methanesulphonate

Methanesulphonyl chloride (12.7 g) was added dropwise to a stirred solution of 3-(2,3-dihydro-2-benzofuranyl) propanol (15.0 g), triethylamine (12.7 g) in dichloromethane (150 mls-dry) at 0° C. under nitrogen. After 24 hours the organic phase washed successively with 5 N hydrochloric acid solution (1×50 mls), saturated sodium bicarbonate solution (1×50 mls) and saturated brine (1×50 mls).

The organic layer was dried over anhydrous magnesium sulphate and excess solvent removed in vacuo yielding an oil (15.5 g after column chromatography; silica chloroform). M/e 256.0775 $C_{12}H_{16}O_4S$ requires 256.0769. NMR (CDCl$_3$) (60 MHz) δ1.75 (4H, m); 2.85 (3H, s); 2.50–3.20 (2H, m); 4.15 (2H, t, J=6.0 HZ); 4.65 (1H, m) 6.50–7.10 (4H, m).

(f) 3-(2,3-Dihydro-2-benzofuranyl) propyl bromide 3-(2,3-Dihydro-2-benzofuranyl) propyl methanesulphonate (18 g), lithium bromide (12.2 g) and acetone (150 mls) were mixed and heated under reflux for 1.5 h. The mixture was cooled and evaporated yielding an oily solid. This residue was treated with ether (4×20 mls). After drying the organic phase over anhydrous magnesium sulphate excess solvent was removed in vacuo affording an oil (15 g). This material was checked by t.l.c. and was carried through to the next stage. NMR (CDCl$_3$) (60 MH) δ1.90 (4H, m); 2.50–3.50 (4H, m); 4.75 (1H, m); 6.60–7.20 (4H, m).

(g) 3-[2,3-Dihydro-2-benzofuranyl)propyl]-1,3-dithiane-2-carboxylic acid ethyl ester A solution of 3-(2,3-dihydro-2-benzofuranyl)propyl bromide (13.5 g) and 2-carboxy-1,3-dithiane (10.8 g) in dimethylformamide (60 mls) was added dropwise at 0° C. to a stirred suspension of 80% NaH (previously washed with petroleum ether) (1.7 g) in toluene (25 mls)/dimethylformamide (40 mls) under nitrogen. Gas was evolved and after five minutes a solid precipated. An additional quantity of toluene-dimethylformamide (100 mls of a 1:1 solution) was added to make the mixture mobile. After one hour the temperature was raised to room temperature and the mixture stirred overnight.

The resulting suspension was poured into water (500 mls) and extracted with ether (4×100 mls). The organic phase was dried over anhydrous magnesium sulphate and excess solvent removed in vacuo yielding an oil (17 g). NMR (CDCl$_3$) (60 MHz) δ1.30 (3H, t, J=7 Hz); 1.80 (4H,m); 2.20–3.50 (10H, m); 4.00 (2H, q, J=7 Hz); 4.50 (1H, m); 6.70 (4H, m).

(h) 2,3-Dihydro-α-oxo-2-benzofuran-pentanoic acid ethyl ester

3-[2,3-Dihydro-2-benzofuranyl)propyl]-1,3-dithiane-2-carboxylic acid ethyl ester (8.0 g) dissolved in acetonitrile (15 mls) was added rapidly to a stirred solution of N-chlorosuccinimide (120 g) and silver nitrate (17.6 g) in 80% acetonitrile-water at 25° C. After 10 minutes saturated solutions of sodium sulphite (50 mls), sodium carbonate (50 mls) and brine were added successively at one minute intervals. To this mixture, a solution of hexane-dichloromethane (1:1, 250 mls) was added followed by filtration through celite. The organic phase of the filtrate was separated and dried over anhydrous magnesium sulphate. Removal of the solvent gave an oil (5.0 g). The unstable product was used immediately in the next stage. M/e M+ 262.

NMR (CDCl$_3$) (60 MHz) δ1.25 (3H, t, J=7 Hz); 1.70 (4H, m); 2.60–3.50 (4H, m); 4.20 (2H, q, J=7 Hz); 4.70 (1H, m); 6.80 (4H, m).

(i) N-[N-[[4-2,3-Dihydro-2]-benzofuranyl)-1-(ethoxycarbonyl)]butyl]-(S)-alanyl]-(S)-proline

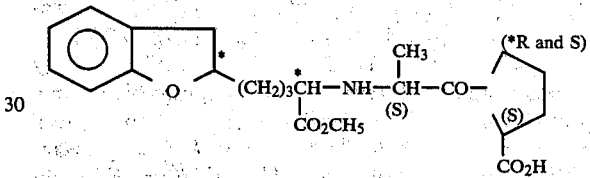

A solution of 2,3-dihydro-α-oxo-2-benzofuranpentanoic acid ethyl ester (5.0 g) in dry ethanol (40 mls) containing powdered activated 4 Å molecular sieves (17 g) was treated with (S)-alanyl-(S)-proline (1.78 g) and then stirred at 25° C. under nitrogen for 1.5 hours. Sodium cyanoborohydride (0.6 g) was added portionwise over 30 hours, and after 48 hours the solution was filtered and evaporated to dryness.

The residue was shaken with saturated sodium bicarbonate solution and chloroform, separated and the aqueous phase washed with chloroform (2×20 ml). The aqueous solution was acidified with 10% citric acid solution until p.H 3.5 and then extracted with chloroform (4×20 mls). The organic phase was dried over anhydrous magnesium sulphate and excess solvent removed in vacuo yielding an oil. Purification by chromatography (silica, 20% methanol-80% chloroform) gave a pale yellow solid (0.5 g). M/e M-H$_2$O, 414.

NMR(CDCl$_3$) (80 MHz) δ1.25 (6H, t, J=8.0 Hz); 1.50–2.50 (8H, m); 2.50–3.90 (8H, n); 4.20 (2H, q, J=8 Hz); 4.40–5.0 (2H, m); 6.60–7.20 (4H, m). $[\alpha]_D^{26} = -53.8°$ C. C=2.00 in methanol.

PHARMACOLOGICAL DATA

1. In vivo test for inhibition of angiotensin converting enzyme

The compounds of examples 1 (d) and 2(i) were each tested in anaesthetised rats for their ability to reduce the pressor responses to angiotensin I, but not those to angiotensin II.

The dose of angiotensin I was 300 ng/kg (iv) and the dose of angiotensin II was 100 ng/kg (iv).

The results given below are the mean of those obtained with at least two rats.

| Compound | Dosage (mg/kg, iv) | % R |  |  |  |  |  |
|---|---|---|---|---|---|---|---|
|  |  | 1 | 5 | 15 | 20 | 30 | 40 | 50 |
| Ex. 1(d) | 0.1 | 51 | 28 | 19 | 24 | 5 | — | — |
|  | 0.3 | 36 | 59 | 67 | 59 | 57 | 47 | 44 |
|  | 1.0 | 45 | 69 | 61 | 61 | 65 | 59 | 55 |
| Ex. 2(i) | 0.1 | 30 | 76 | 76 | 71 | 71 | 60 | 47 |

'I' is the increase in diastolic blood pressure (mm Hg) to angiotensin I (control response).

'%R' is the percentage reduction in control angiotensin I response after the intervals (min) from dosage.

In the same rats each dose of the compounds of Examples 1(a) and 2(i) augmented the pressor responses to angiotensin II.

From the above results, it is concluded that the compounds of Examples 1(a) and 2(i) reduce the pressor responses to angiotensin I but not those to angiotensin II and thus inhibit angiotensin converting enzyme.

2. Anti-Hypertensive Activity

Systolic blood pressures were recorded by a modification of the tail cuff method described by I M Claxton, M G Palfreyman, R H Poyser and R L Whiting, European Journal of Pharmacology, 37, 179 (1976), A W+W BP recorder, model 8005 was used to display pulses. Prior to all measurements rats were placed in a heated enviroment (33.5±0.5° C.) before transfer to a restraining cage. Each determination of blood pressure was the mean of at least 6 readings. Spontaneously hypertensive rats (ages 12–18 weeks) with systolic blood pressures 170>mmHg were considered hypertensive.

| Compound of Example | Time post dose hours | % Change in systolic blood pressure | % Change in heart rate |
|---|---|---|---|
| 1 (d) |  |  |  |
| 6 rats |  |  |  |
| Dose 100 mg/kg po | 1 | −16 ± 2 | −1 ± 1 |
|  | 2 | −26 ± 2 | 0 ± 2 |
| Initial Blood | 4 | −24 ± 2 | −2 ± 1 |
| Pressure 244 ± 3 | 6 | −25 ± 2 | −4 ± 2 |
| Initial Heart | 24 | −14 ± 2 | −4 ± 2 |
| Rate 488 ± 6 |  |  |  |
| 2 (i) |  |  |  |
| 6 rats |  |  |  |
| Dose 100 mg/kg po | 1 | −10 ± 3 | 6 ± 2 |
|  | 2 | −6 ± 3 | 7 ± 2 |
| Initial Blood | 4 | −15 ± 2 | 8 ± 2 |
| Pressure 218 ± 4 | 6 | −24 ± 3 | 11 ± 2 |
| Initial Heart | 24 | −13 ± 5 | 7 ± 3 |
| Rate 440 ± 13 |  |  |  |

Conclusion

The compounds of Examples 1(d) and 2(i) lower the blood pressure of spontaneously hypertensive rats from 1–24 hour post dose, without affecting the heart rate.

Toxicity

No toxic effects were observed in these tests.
What we claim is:
1. A compound of formula (I),

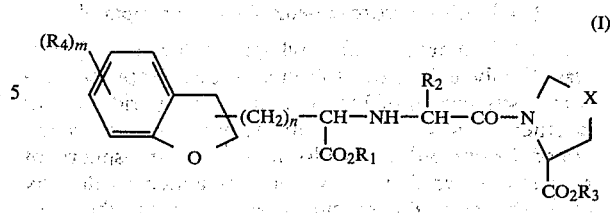

or a pharmaceutically acceptable salt thereof, wherein:
m is 0 to 3;
n is 1 to 5;
$R_1$ is hydrogen or $C_{1-6}$ alkyl;
$R_2$ is hydrogen, $C_{1-4}$ alkyl, $-(CH_2)_p-NH_2$ wherein p is 1 to 4, or $-NHCOR_5$, wherein $R_5$ is $C_{1-4}$ alkyl;
$R_3$ is hydrogen or $C_{1-6}$ alkyl
$R_4$ is $C_{1-4}$ alkyl, $C_{1-4}$ alkoxy, halogen or $CF_3$;
and x is $CH_2$ or S.

2. A compound according to claim 1, wherein the dihydrobenzofuranyl moiety is bonded to the rest of the structure at the 2-position.

3. A compound according to claim 2, having the formula (I)'

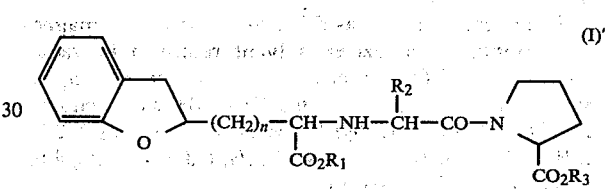

or a pharmaceutically acceptable salt thereof, wherein:
n is 1 or 2 to 5
$R_1$ and $R_3$ are the same or different and each is hydrogen or $C_{1-4}$ alkyl; and
$R_2$ is hydrogen or $C_{1-4}$ alkyl.

4. A compound according to claim 3, wherein:
n is 2 to 5;
$R_1$ is $C_{1-4}$ alkyl;
$R_2$ is $C_{1-4}$ alkyl; and
$R_3$ is hydrogen.

5. A compound according to claim 1 wherein the asymmetric centres of the part structures of formulae (A) and (B) (indicated *):

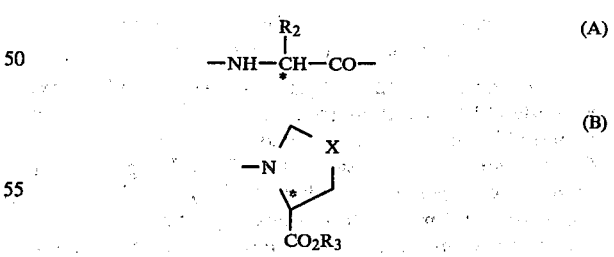

are in the S configuration.

6. N-[N-[[2-(2,3-Dihydro-2-benzofuranyl)-1-(ethoxycarbonyl)]ethyl]-(S)-alanyl]-(S)-proline, or
N-[N-[[4-(2,3-Dihydro-2-benzofuranyl)-1-(ethoxycarbonyl)]butyl]-(S)-alanyl]-(S)-proline or a pharmaceutically acceptable salt thereof.

7. A pharmaceutical composition for the treatment of hypertension which comprises an effective amount of a compound according to claim 1 and a pharmaceutically acceptable carrier.

8. A method of treatment of hypertension in mammals including humans comprising administering to the sufferer a therapeutically effective amount of a composition of claim 7.

9. A compound of claim 1, wherein $R_2$ is hydrogen, $C_{1-4}$ alkyl or $-(CH_2)_p-NH_2$ wherein p is 1 to 4.

10. A compound of the formula (II):

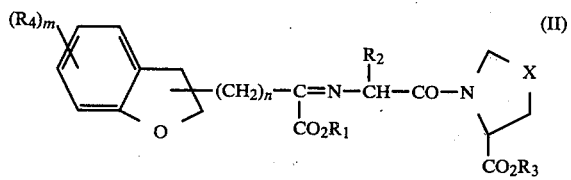

wherein
m is 0 to 3;
n is 1 to 5;
$R_1$ is hydrogen or $C_{1-6}$ alkyl;
$R_2$ is hydrogen, $C_{1-4}$ alkyl, $-(CH_2)_p-NH_2$ wherein p is 1 to 4, or $-NHCOR_5$ wherein $R_5$ is $C_{1-4}$ alkyl;
$R_3$ is hydrogen or $C_{1-6}$ alkyl;
$R_4$ is $C_{1-4}$ alkyl, $C_{1-4}$ alkoxy, halogen or $CF_3$; and
X is $CH_2$ or S.

11. A compound of the formula (III):

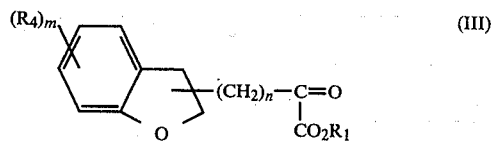

wherein m, n, $R_1$ and $R_4$ are as defined in claim 10.

12. A compound of the formula (V):

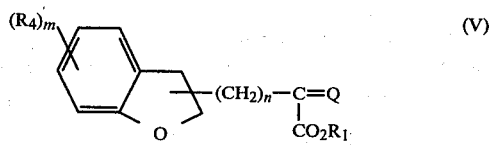

wherein $R_1$ is $C_{1-6}$ alkyl and m, n and $R_4$ are as defined in claim 10, and Q is a carbonyl protecting group.

13. A compound of claim 12, wherein the carbonyl protecting group Q is a ketal or thioketal.

* * * * *